United States Patent [19]
Ozaki et al.

[11] Patent Number: 5,498,377
[45] Date of Patent: Mar. 12, 1996

[54] PRODUCTION OF THERMOPLASTIC POLYURETHANE ELASTOMER TUBE

[75] Inventors: Hidenori Ozaki; Minoru Fuchimoto; Tamotsu Kaide, all of Amagasaki, Japan

[73] Assignee: Mitsubishi Cable Industries, Ltd., Amagasaki, Japan

[21] Appl. No.: 345,740

[22] Filed: Nov. 21, 1994

[30] Foreign Application Priority Data

Nov. 22, 1993 [JP] Japan ................................. 5-291833

[51] Int. Cl.⁶ ............................................. B29C 47/92
[52] U.S. Cl. ................................. 264/40.1; 156/244.13; 264/40.6; 264/40.7; 264/149; 264/166; 264/209.5; 264/288.4; 264/317; 264/DIG. 65; 425/113
[58] Field of Search ................... 264/209.5, 209.1, 264/288.4, 149, 317, 150, 166, DIG. 65, 40.6, 40.7, 40.1, 40.3; 425/113; 156/244.13

[56] References Cited

U.S. PATENT DOCUMENTS

| | | | |
|---|---|---|---|
| 2,561,569 | 7/1951 | Flynn | 264/149 |
| 4,062,834 | 12/1977 | Gilding et al. | 260/77.5 AA |
| 4,321,226 | 3/1982 | Markling | 264/173 |
| 4,764,324 | 8/1988 | Burnham | 264/150 |
| 4,898,702 | 2/1990 | Elkins et al. | 264/166 |
| 5,061,424 | 10/1991 | Karimi et al. | 264/173 |
| 5,063,018 | 11/1991 | Fontirroche et al. | 264/173 |
| 5,096,646 | 3/1992 | Shigemoto et al. | 425/113 |
| 5,100,379 | 3/1992 | Wendell | 264/209.5 |
| 5,409,644 | 4/1995 | Martin et al. | 264/323 |

FOREIGN PATENT DOCUMENTS

| | | | |
|---|---|---|---|
| 0195899 | 10/1986 | European Pat. Off. | |
| 2569114 | 2/1986 | France | |
| 1928843 | 6/1969 | Germany | |
| 62-53363 | 3/1987 | Japan | 264/209.1 |
| 2-198564 | 8/1990 | Japan | |
| 3-153333 | 7/1991 | Japan | 264/209.1 |

OTHER PUBLICATIONS

European Search Report for EP 94118253.7.

*Primary Examiner*—Jeffery R. Thurlow
*Attorney, Agent, or Firm*—Varndell Legal Group

[57] ABSTRACT

A method for producing a thermoplastic polyurethane elastomer tube where the temperature of the mandrel and the extrusion pressure used for extruding a thermoplastic polyurethane elastomer are determined before preparing the tube. The temperature of the mandrel and the extrusion pressure are set to overlap two predetermined temperature ranges. One temperature range permits hot drawing of the tube preform, and the second temperature range provides a tube preform free from the occurrence of bubbles on its surface. After the two temperature and extrusion pressure ranges are determined, a thermoplastic polyurethane elastomer is extruded on the periphery of a heated mandrel under pressure using a mandrel temperature and extrusion pressure where the two predetermined ranges overlap. Thereafter, the mandrel is pulled out to provide a tube preform, and the tube preform is hot drawn to produce a tube having a desired outer diameter. The method of the present invention can provide a thermoplastic polyurethane elastomer tube having a fine hot drawability while overcoming poor appearances due to the occurrence of bubbles or granular structure. In addition, the thermoplastic polyurethane elastomer tube has a stable quality that can be continuously produce, thus increasing the yield thereof.

7 Claims, 2 Drawing Sheets

PRODUCTION OF THERMOPLASTIC POLYURETHANE ELASTOMER TUBE

TECHNICAL FIELD

The present invention relates to an improved production of a tube composed of a thermoplastic polyurethane elastomer (hereinafter also referred to as TPU) by the so-called pressurizing method.

BACKGROUND OF THE INVENTION

The medical tubes such as cannula, catheter etc. are generally inserted into blood vessels (particularly coronary artery), trachea, oviduct, urinary duct and various organs for the injection of liquids, patency of ducts and so on. These medical tubes are mainly made of TPU and the tip thereof is formed thin in a taper shape by hot drawing so as to facilitate insertion thereof into organs etc.

The method for forming a tube inclusive of such medical tube is exemplified by a method wherein TPU extruded from the delivery end of a die head is coated on a mandrel (hereinafter referred to as tubing method). A partial cross section of the die head to be used for the tubing method is shown in FIG. 3. In the tubing method, a mandrel 11 passing along an axial core 10a in a die head 10 is fed to the direction of an arrow b while a TPU 12 delivered from an extruder (not shown) is supplied into the die head 10, defined to a predetermined thickness and extruded from between a die 13 and a nipple 14, as shown in FIG. 3. Since the diameter of the TPU 12 at a delivery end 10b of the die head 10 is greater than that of the mandrel 11 by the thickness of the nipple 14, the TPU 12 falls to cover the mandrel 11.

In the tubing method, however, covering of mandrel 11 by TPU 12 under the open pressure is responsible for possible development of bubbles on the surface of the extruded product of TPU 12. For avoiding the development of the bubbles, the extrusion temperature of TPU 12 needs to be lowered, which in turn results in insufficient melting of TPU 12 to often cause occurrence of a granular structure (development of knob-like humps of from several dozens to several hundred μm in diameter which appear on the surface as a result of the reaction in TPU to form a linear polymer having a higher molecular weight). Accordingly, it is not possible to prevent poor appearance due to the occurrence of bubbles or granular structure by the tubing method.

Another exemplification of the method for forming a tube is a method comprising extrusion-coating a mandrel with TPU in a die head (hereinafter referred to as pressurizing method). A partial cross section of the die head to be used for the pressurizing method is shown in FIG. 2. In the pressurizing method, a mandrel 2 passing along an axial core 1a in a die head 1 is delivered to the direction of an arrow a, while a TPU 3 delivered from an extruder (not shown) is supplied into the die head 1, and the TPU 3 is brought into contact with the mandrel 2 at a delivery end 4a of a nipple 4, as shown in FIG. 2. The mandrel 2 is further fed to the direction of the arrow a, whereby the TPU 2 is defined to a certain thickness by the mandrel 2 and a die 5 and the mandrel 2 covered with the TPU is extruded.

In the pressurizing method, the TPU 3 is coated on the mandrel 2 under pressurization, making a sharp contact with the aforementioned tubing method. Accordingly, the occurrence of bubbles or granular structure is reduced and the appearance of the tube becomes fine. On the other hand, hot drawability of the molding obtained by the pressurizing method is poor. That is, heating of the tip portion of the product to a temperature not lower than the glass transition temperature (Tg) by hot drawing to form same into a taper shape causes clouding of the drawn portion due to microcracks or occurrence of granular structure or even breakage of the portion.

SUMMARY OF THE INVENTION

Under the circumstances, an object of the present invention is to provide a production method of a TPU tube, comprising extruding TPU on the periphery of a mandrel under pressurization, pulling out the mandrel to give a tube preform, and hot drawing the obtained tube preform to produce a tube having a desired outer diameter, the method being free of the problem of poor appearance due to the occurrence of bubbles or granular structure and affording fine hot drawability of the TPU tube.

The present invention is as follows.

A method for producing a thermoplastic polyurethane elastomer tube, comprising (a) extruding a thermoplastic polyurethane elastomer on the periphery of a heated mandrel under pressurization, (b) pulling out the mandrel to give a tube preform, and (c) hot drawing the obtained tube preform to produce a tube having a desired outer diameter, wherein the temperature of the said mandrel and an extrusion pressure on the elastomer are set in such a manner that they fall within the range where a range permitting hot drawing of the tube preform and a range free from the occurrence of bubbles on the tube preform surface overlap, which ranges being determined in advance on the basis of the temperature of the heated mandrel and the extrusion pressure on the elastomer as parameters.

DETAILED DESCRIPTION OF THE INVENTION

Figure 1:
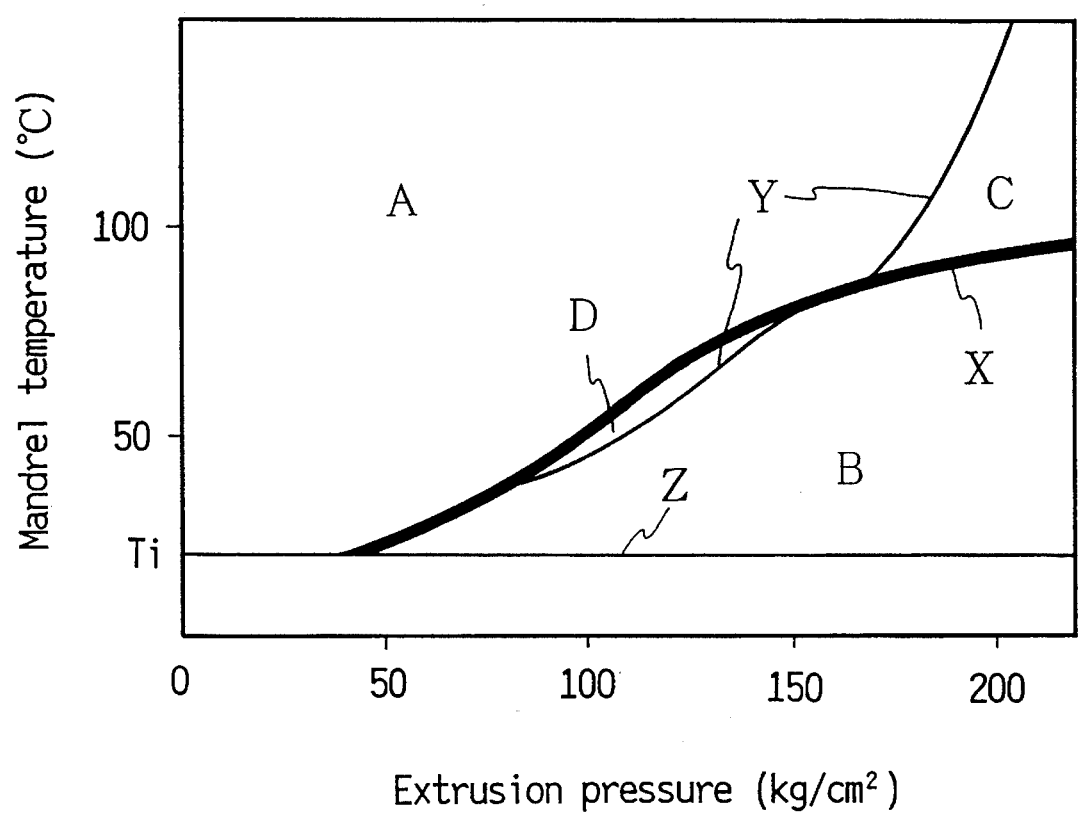
FIG. 1 is a graph showing ranges permitting hot drawing (A, C) and ranges free from occurrence of tube surface bubbles (B, C), which have been determined on the basis of the temperature of mandrel and the extrusion pressure of TPU in the following Examples as parameters, wherein $T_i$ is an initial temperature of the mandrel.
Figure 2:
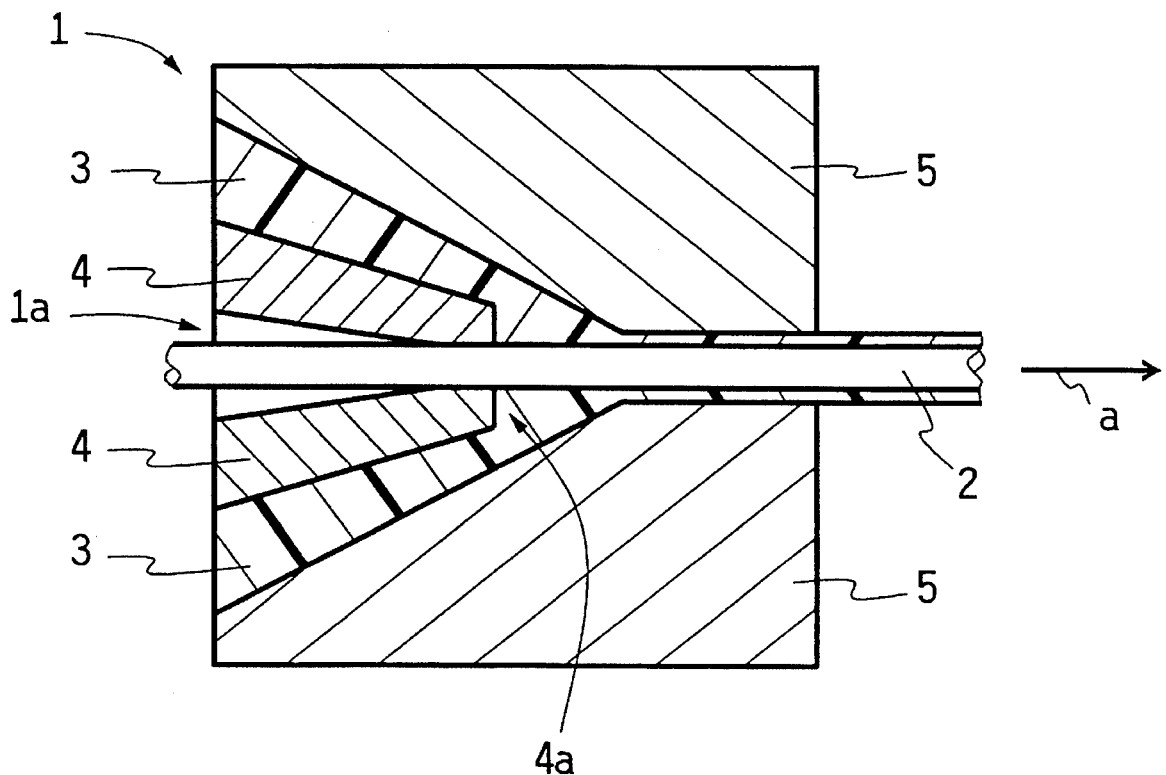
FIG. 2 is a partial cross section of a die head 1 in the pressurizing method, wherein 1a is an axial core, 2 is a mandrel and 3 is TPU.
Figure 3:
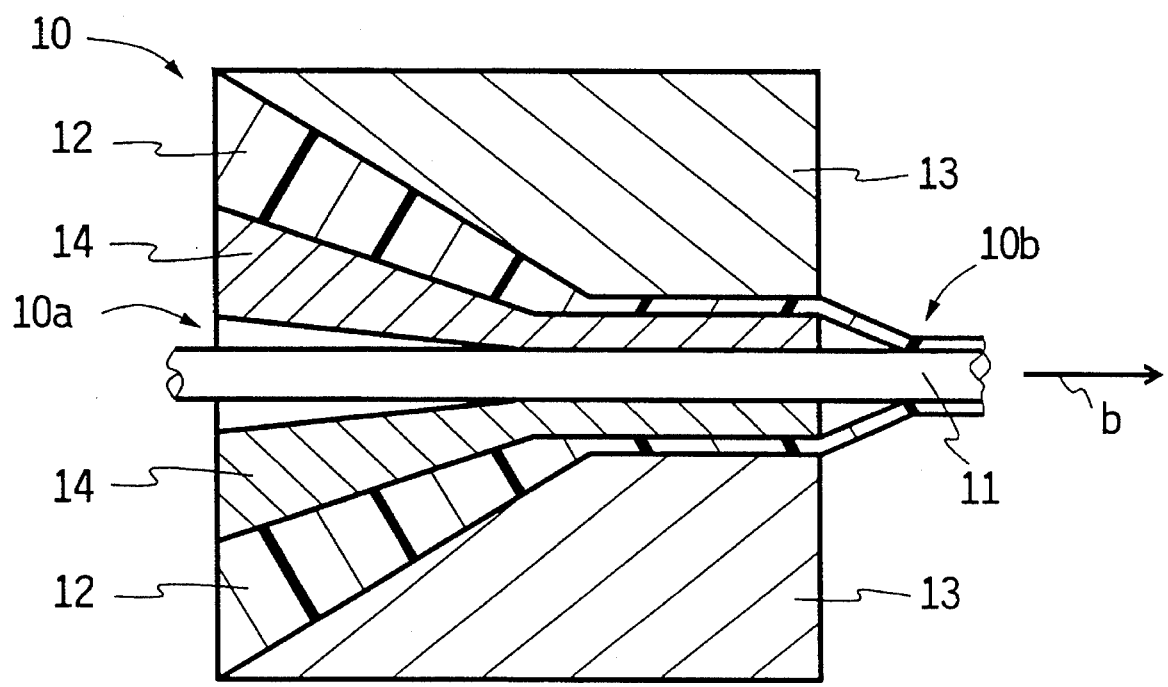
FIG. 3 is a partial cross section of a die head 10 in the tubing method.

The extruder usable in the present invention is subject to no particular limitation insofar as it achieves the objects of the present invention. Examples thereof include screw extruders (e.g. single-screw extruder, multi-screw extruder) and non-screw extruders (e.g. elastic melt extruder, hydrodynamic extruder, ram continuous extruder, roll extruder, gear extruder), with preference given to a single-screw extruder. In the present invention, the extruder excludes a die head having a die.

According to the production of the present invention, TPU is coated on the mandrel in the axial core in the die head. By die head is meant a mold set on a barrel tip of an extruder, which is exemplified by cross head (angle head inclusive) die and spider die. As used herein, the axial core in the die head means the part through which a mandrel to be coated with TPU passes a die head. Examples of the mandrel include annealed copper wire, soft SUS wire and ETFE wire. While the diameter of the mandrel is not limited, it is generally about 0.1–2.0 mm.

TPU is preferably a block copolymer mainly composed of a polyol constituting soft segment (rubber matrix free of hydrogen bond), a chain extender constituting hard segment (a part with hydrogen bond including urethane and urea bonds) and a diisocyanate.

As the polyol, that having at least two active hydrogen atoms, the atom being preferably hydroxyl, in a molecule is used. Examples thereof include polyoxyalkylnene polyol produced by adding alkylene oxide to polyhydric alcohol, such as diol and triol, using aliphatic amine, aromatic amine or the like as an initiator; polyester polyol produced by condensation of acid and alcohol; polytetramethylene glycol, polybutadiene polyol, polypropylene glycol, poly-1,4-butylene glycol adipate, polyethylene glycol adipate, polytetramethylene glycol, polyethylene glycol and addition polymer of bisphenol A with propylene oxide, with particular preference given to an addition polymer of bisphenol A with propylene oxide. The preferable weight average molecular weight of the polyol is about 200–2000. The polyol may be used alone or in combination.

Examples of the chain extender include glycols such as ethylene glycol, 1,4-butanediol and diethylene glycol, amines such as diethanolamine, triethanolamine, tolylenediamine and hexamethylenediamine, polyisocyanates such as TDI (tolylenediisocyanate) adduct of trimethylolpropane and triphenylmethanetriisocyanate, bis(2-hydroxyethyl)hydroquinone, a reaction product of bisphenol A with ethylene oxide and a reaction product of bisphenol A with propylene oxide, which may be used alone or in combination. Particularly preferred is 1,4-butanediol.

The diisocyanate is not particularly limited and those conventionally used for polyurethane may be used. Examples thereof include 2,4- or 2,6-trilenediisocyanate, 4,4'-diphenylmethanediisocyanate, hexamethylenediisocyanate, m- or p-phenylenediisocyanate and isophoronediisocyanate, which may be used alone or in combination. Particularly preferred is 4,4'-diphenylmethanediisocyanate.

The molar ratio of polyol, chain extender and diisocyanate is 1:0.5–2:1.5–3, preferably 1:0.8–1.5:1.8–2.5, more preferably 1:0.9–1.2:1.9–2.2.

The number average molecular weight of TPU is preferably 30000–300000, more preferably 50000–150000.

Where necessary, a catalyst may be used for promoting the reaction for the synthesis of TPU. Examples of the catalyst include tertiary amines such as triethylamine, tetramethylhexamethylenediamine and tolylenediamine, and metal catalysts represented by tin catalysts such as stannous octylate, stannous oleate and dibutyl tin dilaurate, which may be used alone or in combination.

TPU is synthesized by using the above-mentioned polyol, chain extender and diisocyanate and, where necessary, a catalyst. The method for the synthesis is disclosed in, for example, Japanese Patent Unexamined Publication Nos. 293214/1986 and 244341/1988. By changing each component for polyol, chain extender and diisocyanate as appropriate, the glass transition temperature (Tg) of TPU can be optionally varied.

The TPU usable in the present invention preferably has a Tg of –30°–60° C., more preferably 25°–50° C.

When the water content of TPU is high, bubbles due to foaming is liable to be developed. The hygroscopic property of TPU requires reduction of its water content. Accordingly, it is preferable that TPU should be dried at about 80° C. for not less than 5 hours before adding same into an extruder.

In the present invention, the temperature of the heated mandrel refers to that of the mandrel near the inlet of the die head when the mandrel is immediately before delivery into the die head, and the extrusion pressure of TPU is the pressure of TPU at an inlet of the die head (a delivery end of a cylinder through which TPU is supplied into the die head).

The tube preform is a TPU molding having a hollow formed by removing the mandrel from the extrusion molding of TPU which covers the outer periphery of the mandrel, and the range permitting hot drawing of the tube preform is a range determined with the use of the temperature of the heated mandrel and the extrusion pressure of TPU as parameters and refers to the range where drawing of 150% or more is possible at a temperature not less than the glass transition temperature (Tg) of TPU. The range free from the occurrence of bubbles on the surface of the tube preform is also a range determined by the use of the temperature of the heated mandrel and the extrusion pressure of TPU as parameters and refers to the area substantially free of visually observable bubbles or granular structure on the surface of said tube preform. These ranges vary depending on the starting materials for TPU, composition ratio thereof, predetermined thickness of the tube preform and so on, particularly depending on the pseudo crosslinked part (hard segment) of TPU.

According to the present invention, a mandrel is heated to a temperature which falls within the range where the above-mentioned two ranges overlap, and TPU is covered on the mandrel in an extruder and extruded to give an extruded product covering the mandrel. The extruded molding is cooled in a cooling tank etc. It is preferable that the take-up speed of the mandrel should be made as great as possible as long as it does not affect the thickness of the formed product, in view of the possible occurrence of bubbles due to the foaming of dissolved air in the TPU when the process from the extrusion to cooling takes too long. In this way, a tube preform is obtained.

While the thickness of the tube is subject to no particular limitation, it is generally about 0.05–0.4 mm.

The tube of the present invention is preferably used for a medical tube. By the medical tube is meant a tube-like medical instrument (e.g. catheter, cannula, irrigator, bougie) which is inserted in the body of animals inclusive of human for use for tests, observations, diagnoses, treatment and prevention and other purposes. That is, said tube includes various types according to the application area, such as circulatory system, aspiratory system, digestive system, urinary system, genital system and so on, as well as object of use and function thereof, which are exemplified by those having functions such as liquid injection and discharge function, body temperature measuring function, blood pressure measurement and blood examination functions, chemical analysis function or endoscopic function and those equipped with a laser fiber or a balloon. Accordingly, they can be used for mammals inclusive of human (e.g. cow, rabbit, horse, sheep, monkey, dog, cat).

Specific examples of the medical tube include intravenous catheter, cardiac catheter, angiography catheter, vasodilation catheter, thrombus removing catheter, cholangiocatheter, bronchus tube, stomach tube, peridural catheter, esophagus bougie, middle cardiac vein catheter, drainage tube, pancreatic duct tube, cervical canal indwelling catheter, endoscope catheter, urine discharge catheter, nasotracheal oxygen catheter, suction catheter, trocar catheter, ED (enteral diet) catheter and solution infusion tube.

In accord with the method for producing a tube by extrusion molding of the present invention, a tube free of the problem of poor appearance caused by bubbling or granular structure and having fine hot drawability can be obtained by heating a mandrel to a predetermined temperature and extrusion-molding TPU under a specific extrusion pressure, the temperature and the pressure being set in such a manner that they fall within the range, where the range permitting hot drawing of the tube preform and the range free from occurrence of tube preform surface bubbles overlap, the two ranges being determined in advance on the basis of the temperature of heated mandrel and the extrusion pressure of TPU as parameters.

In other words, a mandrel heated to a temperature within the specific range obviates fixing of hard segment of TPU (forming of pseudo crosslinked part), even upon contact of TPU melted within the die head with a mandrel. Furthermore, since TPU is extruded from the die head under an extrusion pressure within a specific range, the pseudo crosslinked part is not formed immediately after TPU has been extruded. Rather, TPU is drawn while the stress is being relaxed, gradually forming a pseudo crosslinked part. In this way, the pseudo crosslinked part and an amorphous part (soft segment) are fixed after the completion of the stress relaxation. Accordingly, when the obtained molding is heated to a temperature not less than the glass transition temperature (Tg) thereof, the soft segment of TPU is released, and drawing becomes possible. While the dissolved air in the TPU is generally released as bubbles by heating mandrel or lowering extrusion pressure of TPU, it is prevented in the molding of the present invention by limiting the temperature of the mandrel and the extrusion pressure of the TPU to a specific range.

According to the conventional pressurizing method, pseudo crosslinked part is formed, increasing partial viscosity, when the TPU melted in the die head contacts the mandrel and the residual stress become great. Consequently, the TPU is drawn, while the pseudo crosslinked part remains fixed, along with the take-up of the mandrel, and the stress relaxation is markedly hindered. In addition, since the amorphous part stays drawn, heating the obtained molding to a temperature not less than the glass transition temperature (Tg) results in the release of the soft segment of TPU, whereas additional drawing is hardly obtained, since the drawing has been already done. In contrast, the pseudo crosslinked part (hard segment) reveals shape memory property and tends to restore to its original state when the pseudo crosslinked part was formed (i.e. when the molten TPU contacted the mandrel). Consequently, clouding of the drawn part due to microcracks or granular structure is developed or even breakage of the part is experienced due to the poor hot drawability.

The present invention is described in more detail by illustrating Examples and Comparative Examples, to which the present invention is not limited.

EXAMPLES 1–6 AND COMPARATIVE EXAMPLES 1–7

A TPU (trade mark MM4510, manufactured by Mitsubishi Jukogyo Kabushiki Kaisha) having a glass transition temperature of about 45° C. was dried at about 80° C. for not less than 5 hours. The TPU was extrusion-coated on an annealed copper wire mandrel under the following extrusion conditions and the mandrel was pulled out. In this way, 50 kinds of molded TPU tubes were obtained.

| | |
|---|---|
| Die diameter | 1.30 mm |
| Nipple diameter | 1.02 mm |
| Temperature of extruder (twin-screw extruder) | 130–225° C. |
| Temperature of die head (cross head) | 205–215° C. |
| Temperature of die | 195–210° C. |
| Temperature of heated mandrel | room temperature–120° C. |

The part 30 cm before the cross head was heated with a hot air heater and the temperature of the part immediately before the inlet of the cross head was measured with a contact type thermometer for temperature control.

| | |
|---|---|
| Extrusion pressure of TPU | 35–234 kg/cm$^2$ |
| Take-up speed of mandrel | 1.6–11.9 m/min |

The take-up speed of the mandrel was appropriately adjusted to make the thickness of the TPU tube about 0.35 mm.

Each TPU tube was examined for hot drawability and appearance and the graph (FIG. 1) was drawn with the use of mandrel temperature and extrusion pressure as parameters. The hot drawability was evaluated by drawing the tube while heating with hot air (85° C.), and appearance was evaluated by the possible granular structure or bubbles which were confirmed with a 4-magnification magnifier. In FIG. 1, a thick line X is a border line between the area which permits drawing of 150% or more at a temperature of not less than Tg of TPU and the area which does not, and the area above the line X is the former (drawing of 150% or more attainable) and the area below the line is the latter (drawing of 150% or more unattainable). A thin line Y is a border line indicating the range free from the occurrence of surface bubbles, which defines poor and fine appearances, wherein the area below the line Y indicates the range of fine appearance and the area above the line indicates the range of poor appearance.

As shown in FIG. 1, four areas A to D were defined by the thick line X, the thin line Y and the line Z designating $T_i$. That is, the area A indicates the range where drawing of 150% or more was possible, whereas the appearance was poor; the area B indicates the range where drawing of 150% or more was not possible, whereas the appearance was fine; the area C indicates the range where drawing of 150% or more was possible and the appearance was fine; and the area D indicates the range where drawing of 150% or more was not possible and the appearance was poor.

TPU tubes were prepared at a temperature (°C.) and under an extrusion pressure (kg/cm$^2$) as shown in Table 1 and hot drawability and appearance were examined as noted above. The results are shown in Table 1. In Table 1, ◯ under hot drawing means that the drawing to 150% or more was possible and X means that the drawing to 150% or more was not possible, and ◯ under appearance means fine and X means poor. The conditions other than the temperature of the mandrel and the extrusion pressure were as defined above.

TABLE 1

| | Test item | | Evaluation item | |
|---|---|---|---|---|
| | Heating temperature | Extrusion pressure | Hot drawing | Appearance |
| Example 1 | 85 | 166 | ○ | ○ |
| Example 2 | 90 | 186 | ○ | ○ |
| Example 3 | 95 | 220 | ○ | ○ |
| Example 4 | 110 | 215 | ○ | ○ |
| Example 5 | 130 | 200 | ○ | ○ |
| Example 6 | 140 | 200 | ○ | ○ |
| Comp. Ex. 1 | 70 | 75 | ○ | X |
| Comp. Ex. 2 | 110 | 131 | ○ | X |
| Comp. Ex. 3 | 120 | 143 | ○ | X |
| Comp. Ex. 4 | 40 | 135 | X | ○ |
| Comp. Ex. 5 | 50 | 145 | X | ○ |
| Comp. Ex. 6 | 70 | 140 | X | ○ |
| Comp. Ex. 7 | 50 | 110 | X | X |

As is evident from the above-mentioned Examples, the hot drawability and appearance of a TPU tube produced by the pressurizing method for extrusion molding become excellent by producing the tube at a mandrel temperature and under an extrusion pressure which have been set in such a manner that they fall within the area (C) where the ranges permitting hot drawing (A and C) and the ranges free from occurrence of surface bubbles (B and C) overlap, the ranges being determined in advance on the basis of the temperature of the mandrel and the extrusion pressure of TPU as parameters.

The conventional pressurizing method and the tubing method have narrow range of optimal conditions and poor reproducibility. Accordingly, variation of the conditions such as the take-up speed of the mandrel and the extrusion pressure results in poor hot drawability or poor appearance of the TPU tube, making it difficult to obtain a TPU tube satisfying the both requirements. As shown in the above-mentioned Examples, the overlapped area (area C) is large as compared with the area obtained by the conventional methods. According to the present invention, reproducibility becomes fine, continuous production of the molded products having stable quality can be done and the yield of the molded products can be increased.

The production of a tube by way of the extrusion molding of the present invention resolves the problem of poor appearance due to the occurrence of bubbles or granular structure and provides a TPU tube having fine hot drawability. The present invention is advantageous in that the reproducibility is fine, the molded products having stable quality can be produced continuously and that the yield of the molded products can be increased.

What is claimed is:

1. A method for producing a thermoplastic polyurethane elastomer tube, comprising:

(a) determining a first range for mandrel temperature and extrusion pressure that provides a preform tube having a surface free of bubbles and a second range for mandrel temperature and extrusion pressure that permits hot drawing of said preform tube, (b) extruding a thermoplastic polyurethane elastomer on the periphery of a heated mandrel under pressure, while maintaining said mandrel and said pressure respectively at a temperature and at an extrusion pressure where said first and second ranges overlap, (c) pulling out the mandrel to give said tube preform, and (d) hot drawing the obtained tube preform to produce a tube having a desired outer diameter.

2. The method of claim 1, wherein the thermoplastic polyurethane elastomer comprises a polyol, a chain extender and a diisocyanate at a molar ratio of 1:0.5–2:1.5–3.

3. The method of claim 2, wherein the molar ratio is 1:0.8–1.5:1.8–2.5.

4. A method for producing a thermoplastic polyurethane elastomer tube, comprising:

(a) extruding a thermoplastic polyurethane elastomer on a periphery of a heated mandrel under pressure, (b) pulling out said mandrel to give a tube preform, (c) repeating steps (a) and (b) at different temperatures for said mandrel and at different extrusion pressures and forming a plurality of tube preforms, (d) determining a first temperature range for said mandrel and a first extrusion pressure range where said tube preforms have a surface free of bubbles, (e) hot drawing at least a portion of said tube preforms of step (c) and determining a second temperature range for said mandrel and a second extrusion pressure range that permits hot drawing of said tube preforms by a predetermined amount, (f) preparing at least one additional tube preform by repeating steps (a) and (b), while maintaining said mandrel and said pressure respectively within a range where said first and second temperature ranges and first and second extrusion pressure ranges overlap, and (g) hot drawing said at least one additional tube perform of step (f) to produce a tube having a desired outer diameter.

5. The method of claim 4, wherein said predetermined amount in step (e) is 150% or more.

6. The method of claim 4, wherein the thermoplastic elastomer includes a polyol, a chain extender and a diisocyanate at a molar ratio of 1:0.5–2:1.5–3.

7. The method of claim 6, wherein the molar ratio is 1.08–1.5:1.8–2.5.

* * * * *